United States Patent [19]
Barnet et al.

[11] Patent Number: 6,165,456
[45] Date of Patent: *Dec. 26, 2000

[54] SHAVING COMPOSITIONS

[75] Inventors: Alfred G. Barnet, Hingham; Merrill R. Mezikofsky, Wakefield, both of Mass.

[73] Assignee: The Gillette Company, Boston, Mass.

[ * ] Notice: This patent is subject to a terminal disclaimer.

[21] Appl. No.: 08/241,524

[22] Filed: May 12, 1994

Related U.S. Application Data

[63] Continuation of application No. 07/645,938, Jan. 25, 1991, Pat. No. 5,326,556.

[51] Int. Cl.$^7$ ..................................................... A61K 7/15
[52] U.S. Cl. ................................. 424/73; 424/45; 424/47; 424/401; 424/486; 514/557; 514/772.4; 514/788.1; 514/944; 574/945; 574/974
[58] Field of Search .................................. 424/401, 486, 424/45, 47, 73; 514/788.1, 772.4, 724, 557, 944, 945, 974

[56] References Cited

U.S. PATENT DOCUMENTS

| | | | |
|---|---|---|---|
| 3,541,581 | 11/1970 | Monson | 252/90 |
| 3,912,665 | 10/1975 | Spitzer | 521/78 |
| 3,912,666 | 12/1975 | Spitzer | 521/78 |
| 4,089,804 | 5/1978 | Falk | 252/355 |
| 4,405,489 | 9/1983 | Sisbarro | 252/315.4 |
| 4,528,111 | 7/1985 | Su | 252/107 |
| 4,606,913 | 8/1986 | Aronson | 514/937 |
| 4,651,503 | 3/1987 | Anderson, III et al. | 53/440 |
| 4,765,975 | 8/1988 | Iovanni | 424/70 |

OTHER PUBLICATIONS

Harry's Cosmeticology, J.B. Wilkinson & R.J. Moore, eds., Chemical Publishing Co., New York, 7th ed., 1982, pp. 156–175 and 188–189.

Dupont Performance Products, Zonyl Fluorosurfacatants (Dec. 1988).

Amoco Polybutenes, Bulletin 12–L (Jun. 1987).

*Primary Examiner*—Neil Levy
*Attorney, Agent, or Firm*—Stephan P. Williams

[57] ABSTRACT

An improved self-foaming shaving gel is provided which includes water, a water-soluble soap component, and a self-foaming agent, plus a hydrogenated polyisobutene in combination with a fluorosurfactant.

10 Claims, No Drawings

SHAVING COMPOSITIONS

This application is a continuation of application Ser. No. 07/645,938 filed on Jan. 25, 1991, now U.S. Pat. No. 5,326,556.

FIELD OF THE INVENTION

This violation relates to improved shaving preparations of the type dispensed in the form of a gel containing a volatile component that cause the gel to turn into a foam by itself when spread on the skin in preparation for wet shaving, i.e., shaving with a razor blade.

BACKGROUND OF THE INVENTION

The class of shaving preparation referred to herein as a "self-foaming gel" is a lather-producing composition which is capable of being dispensed as a gel that is substantially free from foaming, but which when spread over the skin and beard produces a foam generated by the action of a volatile self-foaming agent. Such compositions generally take the form of an oil-in-water emulsion in which the self-foaming agent, generally a low boiling aliphatic hydrocarbon, solubilizes the oil phase, and the water phase comprises a water soluble soap component so selected that the resulting packaged composition is in the form of a stable gel under ambient conditions.

Such products are typically packaged in an aerosol container with a barrier such as a piston or collapsible bag to separate the self-foaming gel from the propellant required for expulsion and thereby ensure that a homogeneous gel is dispensed, substantially free of bubbles, which can produce a self-generated later of uniform consistency and density throughout the life of the product. Other known packaging forms for self-foaming gels include conventional, i.e., non-barrier, aerosol containers and collapsible tubes, although these less expensive packages have not always been entirely satisfactory due to formulation compromises attendant with their use.

For further description of parameters involved in the formulation of such products, reference may be made, for example, to U.S. Pat. Nos. 3,541,581 and 4,528,111; typical manufacturing processes and equipment are disclosed in, for example, U.S. Pat. Nos. 4,405,489 and 4,651,503.

Self-foaming shaving gels are, as noted, well known in the art and have been commercially available for over twenty years, during which time they have achieved a substantial share of the total market for shave preparations. Users tend to exhibit considerable loyalty to this form of shaving preparation and associate its use with obtaining a close, comfortable shave. Nevertheless, further improvement in performance would be desirable.

SUMMARY OF THE INVENTION

We have now unexpectedly found a significant improvement in certain key performance attributes of shaving gels comprising water, a water-soluble soap component, and a self-foaming agent, which additionally include from about 0.0005 to 0.5 percent by weight of a fluorosurfactant in combination with a hydrogenated polyisobutene. In preferred embodiments of the invention lubricity is enhanced by the inclusion of one or more water-soluble polymers, and the composition may also include such optical components as clarity aids, foam modifiers, humectants, perfumes, colorants, skin conditioners, and emollients.

The major essential components of the shaving gel is about 55–85%, preferably about 65–80% by weight of water, which is preferably deionized or distilled water free of dissolved electrolytes such as salts and acids. The water component is essential to provide adequate solubility for the soap component and compatibility with the other essential ingredients and to provide a stable shaving gel having the desired foaming properties and capable of being readily rinsed from the skin.

The soap component of the composition, for the purposes hereof, may include a water soluble salt of a fatty acid or any of certain, usually synthetic, wetting agents or detergents, or a combination thereof; where both types are used together, the combination is designated the soap component or, simply, the soap. All of these materials are well known in the art.

The water-soluble fatty acid salts may be performed or formed in situ by reacting a basic material such as triethanolamine, sodium hydroxide, or potassium hydroxide with a higher fatty acid such as stearic, palmitic, myristic, oleic, coconut oil fatty acids, and mixing thereof. The nature of the soap or detergent used is not critical but, in combination with the other components of the composition and their relative proportions, as is known in the art, has an effect on the properties of the shaving gel product of the invention and the later produced. Particularly preferred are triethanolamine soaps of stearic and palmitic acids, though many and various animal and vegetable oil soaps and blends thereof are suitable for use in the practice of the invention The wetting agents that are useful as the soap component or as a portion of the soap component preferably are nonionic in character, and should be appreciably soluble in the aqueous components of the gel. Numerous such materials are well known in the art. As examples, mention may be made of such wetting agents as water soluble polyoxyethylene ethers of alkyl-substituted phenols and water-soluble polyethoxylated derivatives of fatty alcohols. Particularly good results are obtained with Oleth-20, which when combined at a level of about 4–6% with suitable fatty acid soaps, results in the formation of a shaving gel composition of excellent properties without the need for any additional thickener or gelling agent. (Chemical names as used herein follow the system of nomenclature adopted by the Cosmetic, Toiletry and Fragrance Association, Inc.) The soap component constitutes about 5–30%, preferably about 12–25% by weight of the shaving gel.

Another essential ingredient of the self-foaming gel of the present invention is about 0.5–10% and preferably about 1–5% of a volatile self-foaming agent which preferably is a hydrocarbon selected from the group consisting of n-pentane, isopentane, neopentane, n-butane, and isobutane, and mixtures thereof. A blend of isopentane and isobutane in a weight ratio of 3:1 is particularly desirable. Too much self-foaming agent can result in a product that is delivered as a foam, while too little results in greater effort and longer time to generate a foam on the skin.

Fluorosurfactants used in the present formulations are hydrophobic-lipophobic perfluorinated compounds which can be represented by the formula

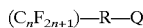

wherein n is an integer from 4 to 18, R is selected from the group consisting of —X—, —Y—O—Z, —Y—S—Z—,

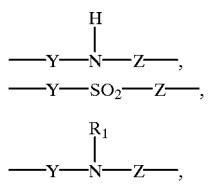

—Y—CONH—Z—, —Y—SO$_2$NH—Z—, wherein Z is (CH$_2$)$_x$, Y is (CH$_2$)$_y$ and Z is (CH$_2$)$_z$, R$_1$ is an alkyl group containing from 1 to 4 carbon atoms, wherein x is an integer from 1 to 6, the terminal (CH$_2$)$_y$ group is attached to the (C$_n$F$_{2n+1}$) portion of the molecule, the terminal (CH$_2$)$_z$ group is attached to the Q portion of the molecule, Y is an integer from 0 to 3, z is an integer from 1 to 3, and Q is selected from the group of —O—CH$_2$CH$_2$O)$_{xH}$, where x=1–10;

—CO$_c$M, where M is an alkali metal (e.g., Na, K. Li);

—N(CH$_3$)$_3$CH$_2$SO$^-$

Commercially available surfactants which fall within the definition of this formula include Zonyl FSA, an anionic fluorochemical surfactant (R$_f$CH$_2$CH$_2$SCH$_2$CH$_2$CO$_2$Li) manufactured by E. I. DuPont de Nemours & Company; Zonyl FSK, an amphoteric fluorochemical surfactant [R$_f$CH$_2$CH(OCOCH$_3$)CH$_2$N$^+$(CH$_3$)$_2$CH$_2$CO$^-_2$] manufactured by E. I. DuPont de Nemours & Company; Zonyl FSN, a nonionic fluorochemical surfactant ([R$_f$CH$_2$CH$_2$O(CH$_2$CH$_2$O)$_x$H] manufactured by E. I. DuPont de Nemours & Company (R$_f$=F (CF$_2$CF$_2$)$_{3-8}$); and Lodyne S-112B—a blend of an anionic fluorochemical sodium sulfonate type and a nonionic fluorochemical synergist of the fluoroalkyl amide type manufactured by Ciba-Geigy. Cationic fluorosurfactants are not preferred, due to compatibility problems with any anionic soap component in the composition. Formulations of the invention contain a small but effective amount of fluorosurfactant, present at from about 0.0005–0.5 percent, preferably from about 0.001–0.1 percent and more preferably from about 0.002–0.01 weight percent of the composition as an active ingredient.

The hydrogenated polyisobutene component is represented by the formula [—CH$_2$—C(CH$_3$)$_2$—]$_n$, where n (the number of repeating units) is about 6 to 24. An example of such material is Cosmetic Grade Panalane L-14E which has an average molecular weight of about 320 daltons (i.e., n=6), from Amoco Chemical Company, Chicago, Ill. Another suitable polyisobutene mixture is available from Nippon Oils under the name Polysynlane. The hydrogenated polyisobutene constitutes about 0.5–5%, preferably about 1–4% by weight of the composition.

The self-foaming shaving gels of the present invention may, as indicated, form suitable gels without the inclusion of any thickener or gelling agent, depending particularly on the selection and concentration of the soap component of the composition. However, such "thickeners" as water-soluble polymers may be incorporated to impart enhanced lubricity to the compositions even without, in particular formulations, performing any thickening function. While water-soluble polymers as a class are useful in providing enhanced lubricity, mention may be made of such materials as copolymers of acrylic acid and a polyallyl sucrose, reaction products of cellulose or glucose with acids or alkylene oxides, natural gums, other synthetic gums, resins, latices, starches, alcohols, and protein gel-formers generally used as thickeners in cosmetic and pharmaceutical preparations. Particularly preferred water-soluble polymers include polyethylene oxide and hydroxyethyl cellulose (the latter sold as various grades of "Natrosol"by Hercules, Inc., Wilmington, Del.). When included, the water-soluble polymer usually comprises 0.01–5%, preferably 0.1–2% by weight of the composition.

Other compatible additives as are well known in the art for use in shaving preparations may also be included in minor proportions so long as they do not adversely affect the properties of the gel. As examples of such additives, mention may be made of humectants, e.g., glycerine, sorbitor, glycereth –26; emollients, e.g. PEG-150 distearate, cocotriglycerides; skin freshening and skin soothing ingredients, e.g. menthol; aloe; lanolin; stability enhancers, e.g., lauramide DEA; perfume; colorants; opacifiers and clarifying agents as desired; and antiseptic agents.

The following Examples illustrate representative self-foaming shaving gel products and are given by way of illustration only and are not to be considered as being limiting. The amounts in the Examples and the claims are in weight percent.

EXAMPLE 1

| CTFA Name | % Active |
|---|---|
| Water | 69.03 |
| Palmitic Acid | 8.17 |
| Oleth-20 | 5.77 |
| Triethanolamine (99%) | 5.00 |
| Isopentane | 2.89 |
| Isobutane | 0.96 |
| Hydrogenated Polyisobutenes (Panalane) | 1.92 |
| Glycereth-26 | 1.92 |
| Lauramide DEA | 1.44 |
| Aloe Vera Gel | 0.96 |
| Fragrance | 0.96 |
| PEG-150 Distearate | 0.48 |
| PEG-14M (polyethylene oxide) | 0.29 |
| Hydroxyethyl Cellulose (Natrosol 250 HHR) | 0.19 |
| Acetic Acid (vehicle for fluorosurfactant) | 0.005 |
| Fluorosurfactant (Zonyl FSK) | 0.005 |
| Colorant | 0.0006 |

Procedure: Form the aqueous phase by dissolving into the water at room temperature the Glycereth-26, hydroxyethyl cellulose, and PEG-14M. Heat to 80°–85° C., and add the palmitic acid, then triethanolamine with mixing. Form an oil phase by mixing, at 55° C., the Oleth-20, PEG-150 distearate, hydrogenated polyisobutene, and lauramide DEA. Add the oil phase with thorough mixing to the aqueous phase maintained at 80° C. Cool to 40° C., and add the fluorosurfactant, aloe gel, fragrance, and dye. Mix and cool to room temperature; then blend with the mixed isopentane/isobutane and package in a barrier-type aerosol container.

The self-foaming shaving gel of Example I was tested against a commercial self-foaming gel well established in the marketplace, in a standard "crossover" test in which test panelists shave full face with one product for one week and then for another week with the other product. The identity of the test products is concealed from the test panelists. In this test the product of Example I was significantly preferred (at the 95% confidence level or better) in the key attributes of beard softening, avoidance of nicks and cuts, razor glide, and perception of facial cleanliness after shaving.

| CTFA Name | % Active |
|---|---|
| Water | 73.82 |
| Stearic Acid | 7.69 |
| Oleth-20 | 5.76 |
| Triethanolamine (99%) | 3.37 |
| Lauramide DEA | 2.88 |
| Isopentane | 2.88 |
| Isobutane | 0.96 |
| Hydrogenated Polyisobutene (Panalane) | 1.42 |
| Fragrance | 0.72 |
| Hydroxyethyl Cellulose (Natrosol 250 HR) | 0.39 |
| Coco-triglyceride | 0.10 |
| Fluorosurfactant (Zonyl FSK) | 0.005 |
| Acetic Acid (vehicle for flourosurfactant) | 0.005 |
| Colorant | 0.0005 |

The procedure follows the process described in Example 1.

While particular embodiments of the invention have been shown and described, various modifications will be apparent to those skilled in the art, and therefore it is not intended that the invention be limited to the disclosed embodiments or to details thereof, and departures may be made therefrom within the spirit and scope of the invention.

What is claimed is:

1. In a shaving composition in the form of a self-foaming gel comprising water, a water-soluble soap, and a volatile hydrocarbon self-foaming agent, the improvement wherein said shaving composition additionally comprises a fluorosurfactant and a hydrogenated polyisobutene.

2. The shaving composition of claim 1 wherein the hydrogenated polyisobutene comprises about 0.5 to 5 percent by weight of the composition and the fluorosurfactant comprises about 0.0005 to 0.5 percent by weight of the composition.

3. The shaving composition of claim 2 wherein the fluorosurfactant comprises about 0.001 to 0.1 percent by weight of the composition.

4. The shaving composition of claim 3 wherein said water soluble soap comprises a sodium, potassium or triethanolamine salt of a fatty acid selected from stearic, palmitic, myristic, oleic, and coconut oil fatty acids, and mixtures thereof.

5. The shaving composition of claim 4 wherein the fluorosurfactant comprises about 0.0002 to 0.01 percent by weight of the composition.

6. The shaving composition of claim 5 wherein the hydrogenated polyisobutene has an average molecular weight of about 320 daltons.

7. The shaving composition of claim 6 additionally comprising about 0.01 to 5 percent by weight of a water-soluble polymer.

8. The shaving composition of claim 5 wherein the fluorosurfactant is selected from $R_fCH_2CH_2SCH_2CH_2CO_2Li$, $R_fCH_2CH(OCOCH_3)CH_2N^+(CH_3)_2CH_2CO_2^-$ and $R_fCH_2CH_2O(CH_2CH_2O)_xH$ wherein $R_f$ is $F(CH_2CF_2)_{3-8}$.

9. The shaving composition of claim 8 wherein the hydrogenated polyisobutene has an average molecular weight of about 320 daltons.

10. The shaving composition of claim 6 additionally comprising about 4 to 6% of a water soluble polyethoxylated fatty alcohol.

\* \* \* \* \*